(12) United States Patent
Tongra et al.

(10) Patent No.: US 12,036,193 B2
(45) Date of Patent: Jul. 16, 2024

(54) SYNERGISTIC BIOACTIVE COMPOSITIONS FOR TREATING NEUROLOGICAL DISORDERS

(71) Applicant: CELAGENEX RESEARCH (INDIA) PVT. LTD., Maharashtra (IN)

(72) Inventors: Rajendra Prasad Tongra, Jaipur (IN); Dhiraj Dhamane, Kalyan-Thane (IN)

(73) Assignee: CELAGENEX RESEARCH (INDIA) PVT. LTD., Thane (IN)

(*) Notice: Subject to any disclaimer, the term of this patent is extended or adjusted under 35 U.S.C. 154(b) by 0 days.

(21) Appl. No.: 17/608,905

(22) PCT Filed: Sep. 9, 2020

(86) PCT No.: PCT/IN2020/050780
§ 371 (c)(1),
(2) Date: Nov. 4, 2021

(87) PCT Pub. No.: WO2021/048871
PCT Pub. Date: Mar. 18, 2021

(65) Prior Publication Data
US 2022/0296540 A1      Sep. 22, 2022

(30) Foreign Application Priority Data
Sep. 15, 2019   (IN) .............................. 201921019337

(51) Int. Cl.
*A61K 31/155* (2006.01)
*A61K 31/164* (2006.01)
*A61P 25/00* (2006.01)

(52) U.S. Cl.
CPC .......... *A61K 31/155* (2013.01); *A61K 31/164* (2013.01); *A61P 25/00* (2018.01)

(58) Field of Classification Search
None
See application file for complete search history.

(56) References Cited

U.S. PATENT DOCUMENTS 5,677,349 A   10/1997  Gilad et al.
6,150,419 A   11/2000  Fairbanks et al.
(Continued)

FOREIGN PATENT DOCUMENTS

EP    2475352 A1 *  7/2012  ............ A61K 31/05
EP    3 130 336 A1   2/2017
(Continued)

OTHER PUBLICATIONS

Machine translation: WO 2008/019594 (Year: 2008).*
(Continued)

*Primary Examiner* — Bethany P Barham
*Assistant Examiner* — Barbara S Frazier
(74) *Attorney, Agent, or Firm* — Maschoff Brennan

(57) ABSTRACT

The present invention disclosed herein relates to synergistic bioactive compositions for treating neurological disorders. Particularly, the invention relates to anti-ischemic nutritional compositions. More particular, the invention relates to synergistic, efficient, nutritional compositions for treating cerebral ischemia comprising therapeutically active exogenous combination of a decarboxylated L-arginine called agmatine (AGM) and a bio-optimized palmitoylethanolamide (Bio-PEA) and salts thereof, wherein the decarboxylated L-arginine salt i.e., agmatine sulfate and bio-optimized palmitoylethanolamide (PEA) are present in a weight ratio of 1:0.1 to 1:5 along with pharmaceutically acceptable excipients.

3 Claims, 7 Drawing Sheets

(56) References Cited

U.S. PATENT DOCUMENTS

| | | | |
|---|---|---|---|
| 7,635,691 B2 | 12/2009 | Foguet et al. | |
| 8,916,612 B2 * | 12/2014 | Gilad | A23C 9/13 |
| | | | 514/579 |
| 9,993,447 B2 | 6/2018 | Alevizache et al. | |
| 2015/0005387 A1 | 1/2015 | Moulinoux | |
| 2015/0182479 A1 | 7/2015 | Glynn et al. | |

FOREIGN PATENT DOCUMENTS

| | | | | |
|---|---|---|---|---|
| WO | 1996/022104 A1 | 7/1996 | | |
| WO | 2001/095897 A1 | 12/2001 | | |
| WO | WO-0195897 A1 * | 12/2001 | ........... | A61K 31/155 |
| WO | 2008/19594 A1 | 2/2008 | | |
| WO | 2011/027373 A1 | 3/2011 | | |
| WO | 2015/138974 A1 | 9/2015 | | |

OTHER PUBLICATIONS

Roundoc Rx, "Nutritional and Botanical Approaches for Peripheral Neuropathy", Alternative and Complementary Therapies, vol. 21, No. 3, pp. 99-105, Jun. 2015 (Year: 2015).*

* cited by examiner

Figure-3 Group 1
| | | | | |
|---|---|---|---|---|
| RA01 | 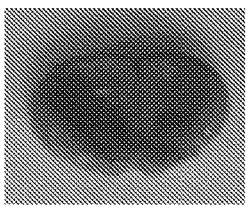 | 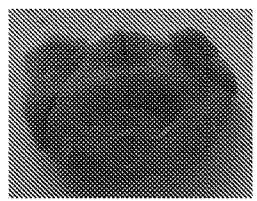 | 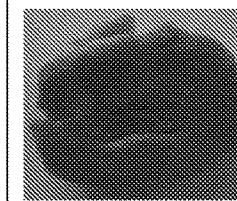 | 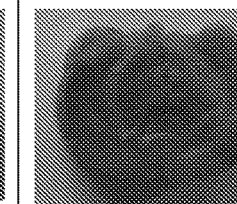 |
| RA02 | 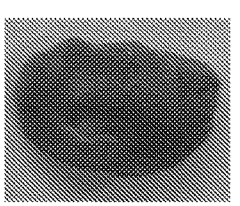 | 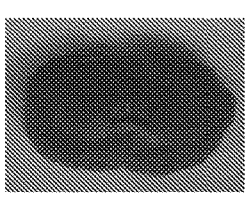 | 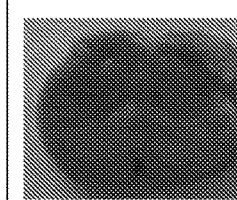 | 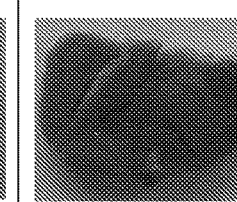 |
| RA03 | 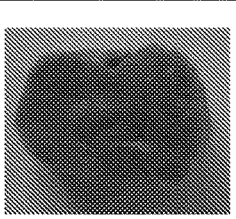 | 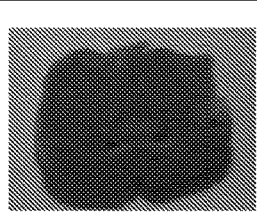 | 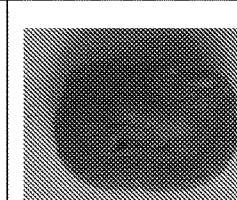 | 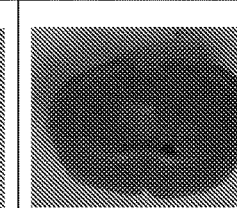 |
| RA04 | 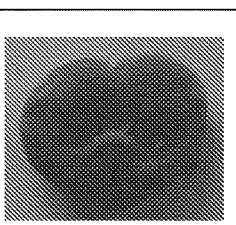 | 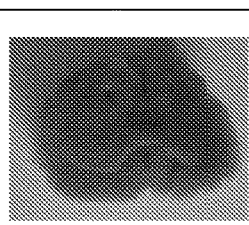 | 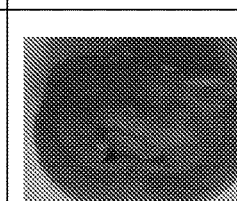 | 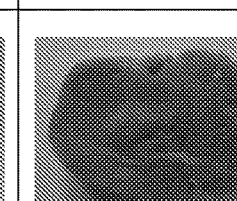 |
| RA05 | 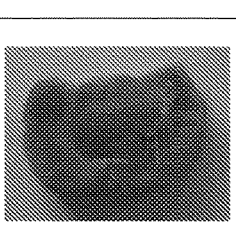 | 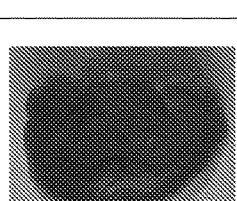 | 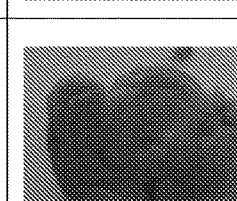 | 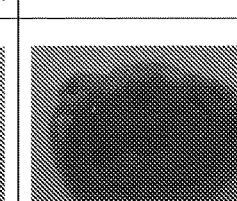 |
| RA06 | 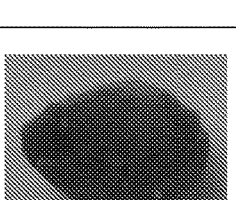 | 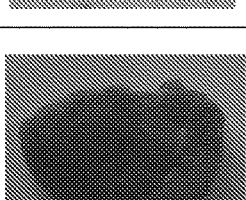 | 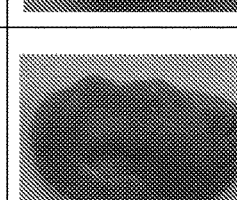 | 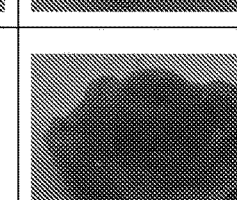 |

Figure-4 Group 2
| | | | | |
|---|---|---|---|---|
| RA01 | 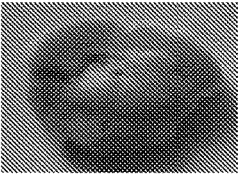 | 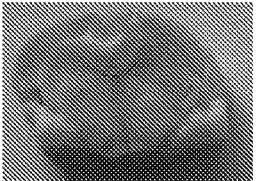 | 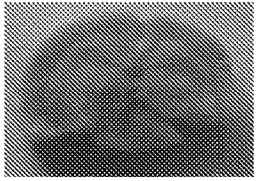 | 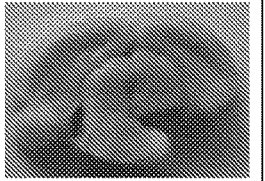 |
| RA02 | 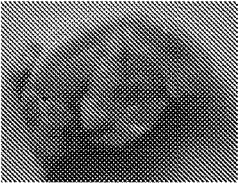 | 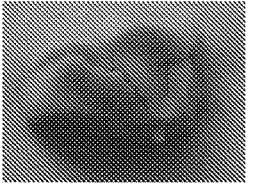 | 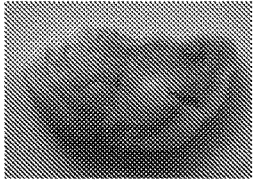 | 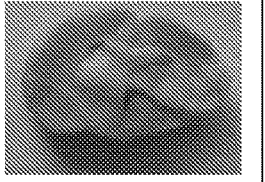 |
| RA03 | 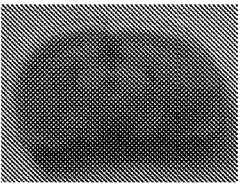 | 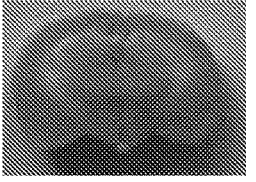 | 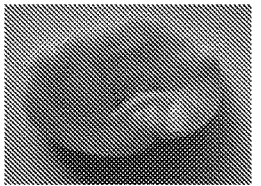 | 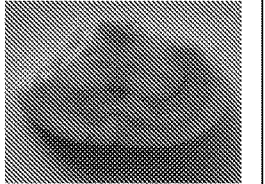 |
| RA04 | 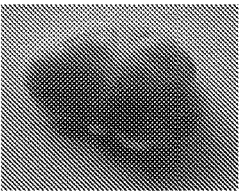 | 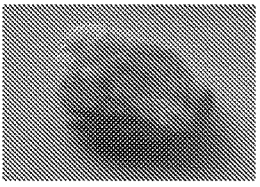 | 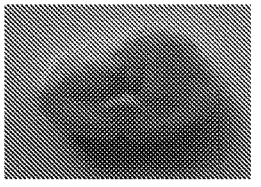 | 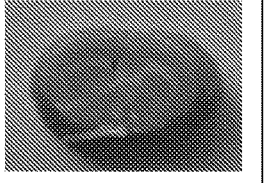 |
| RA05 | 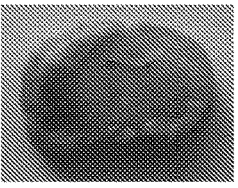 | 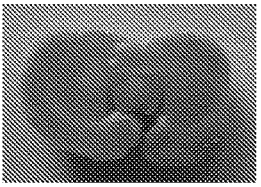 | 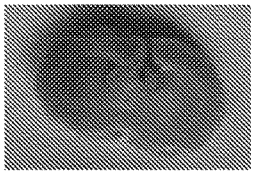 | 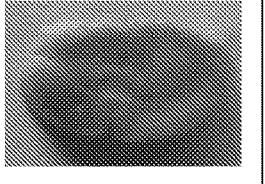 |
| RA06 | 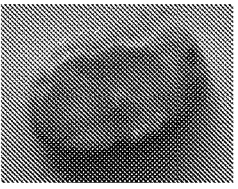 | 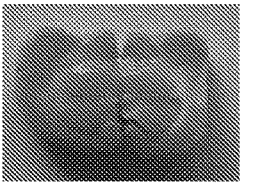 | 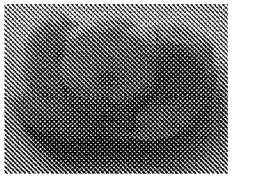 | 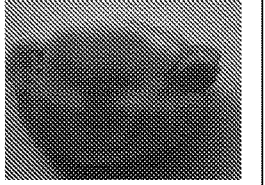 |

Figure-5 Group 3
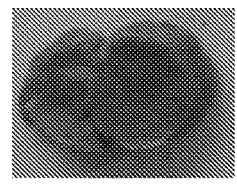
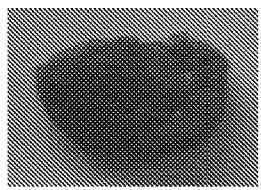
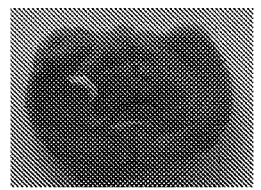
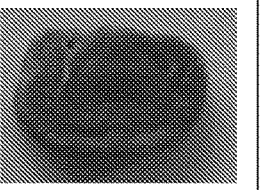
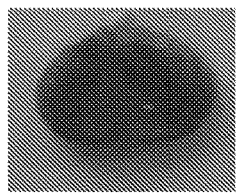
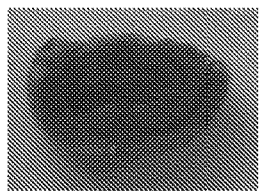
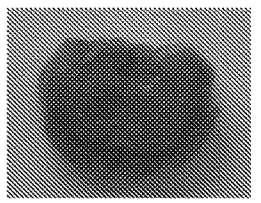
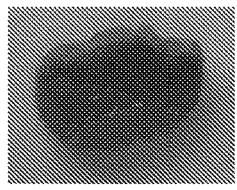
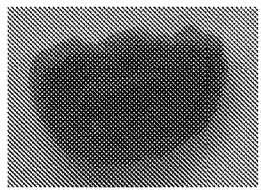
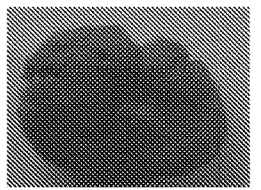
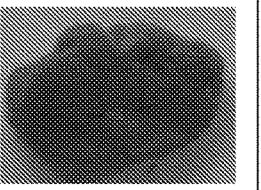
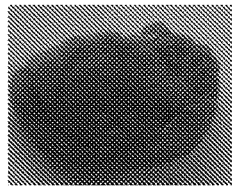
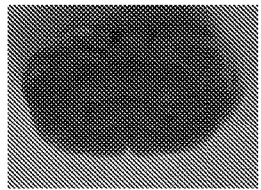
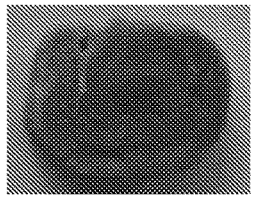
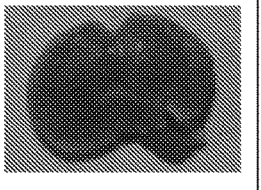
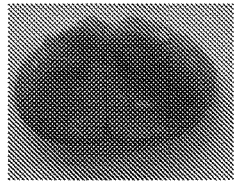
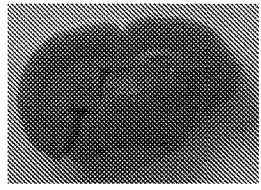
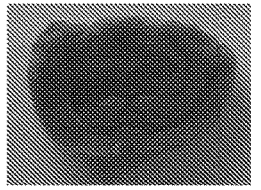
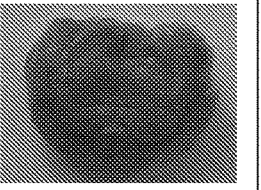
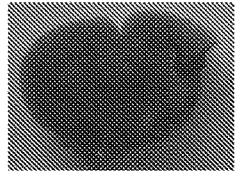
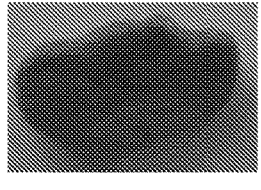
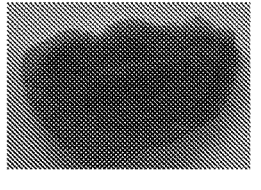
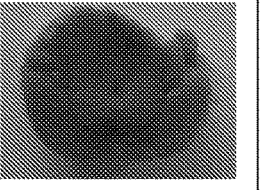

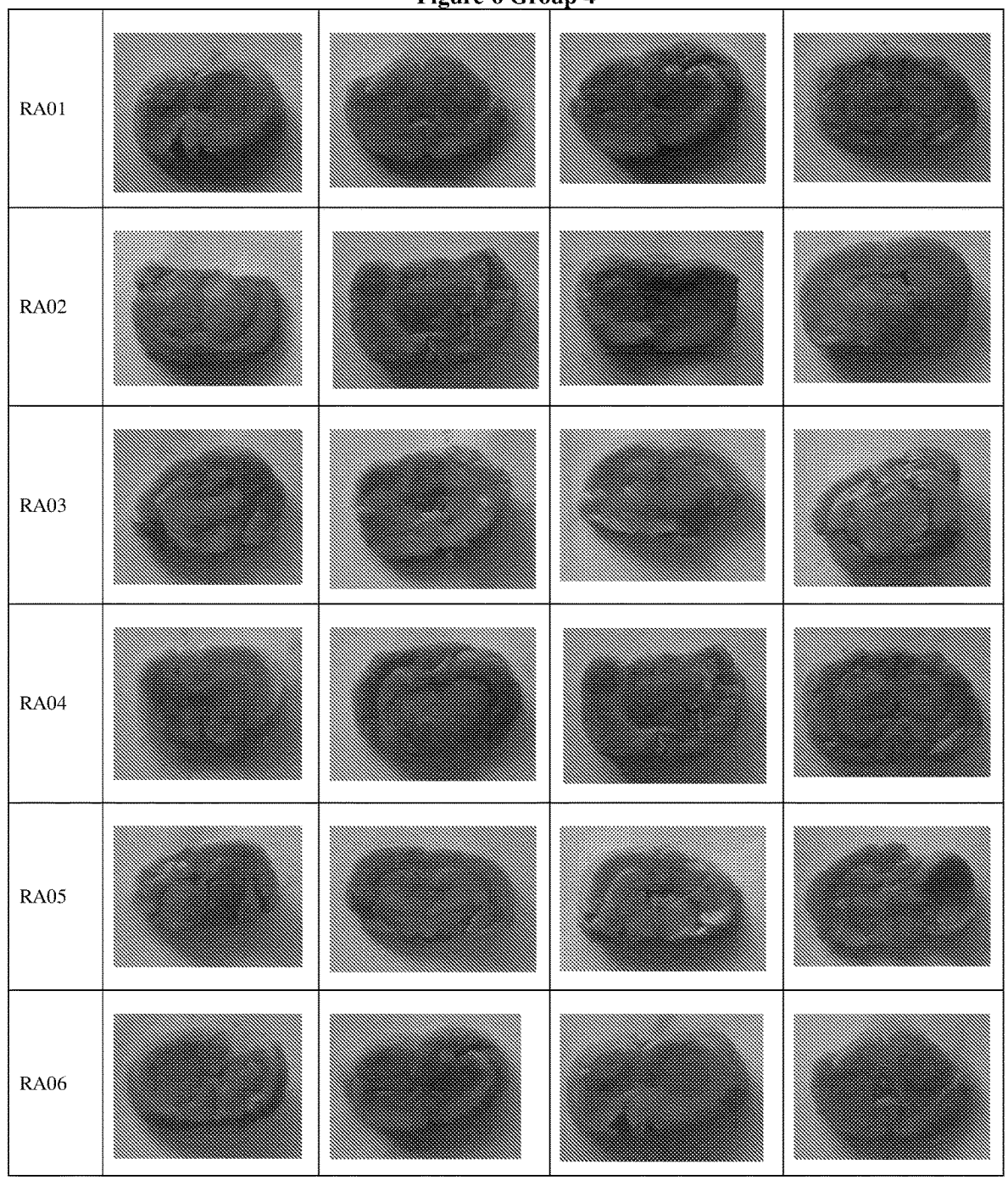
Figure-6 Group 4

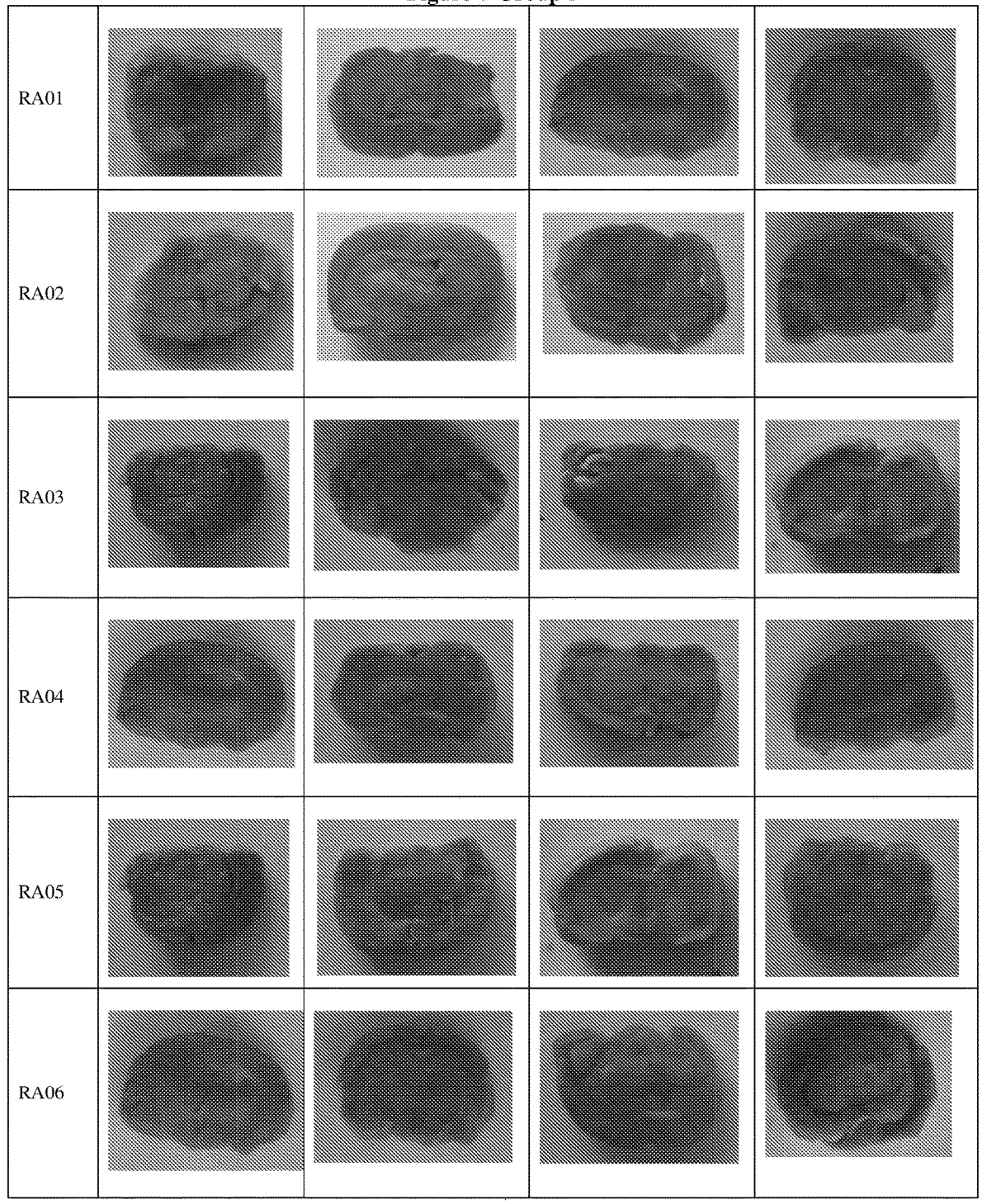

Figure-8 Group 6
| | | | | |
|---|---|---|---|---|
| RA01 | 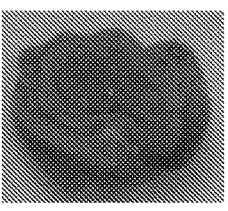 | 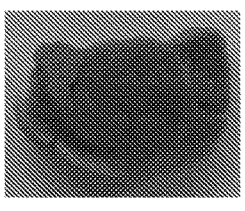 | 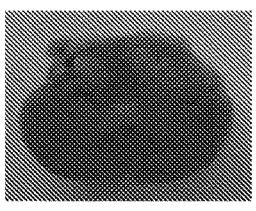 | 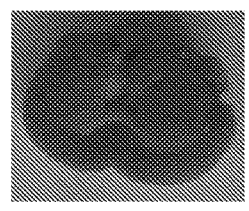 |
| RA02 | 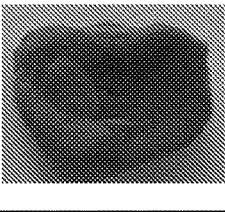 | 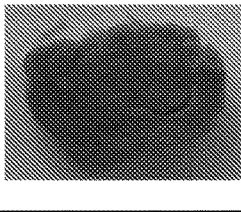 | 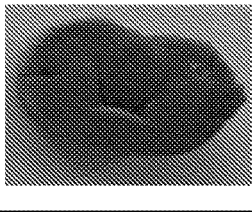 | 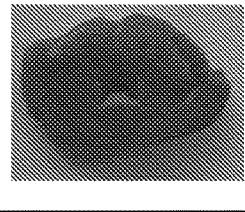 |
| RA03 | 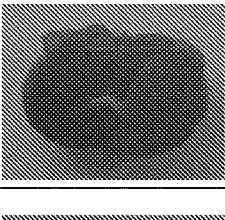 | 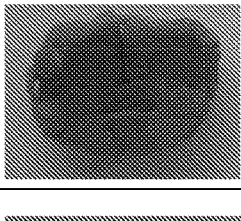 | 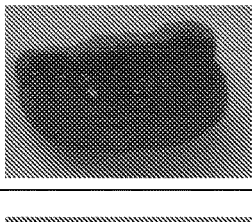 | 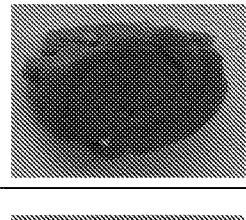 |
| RA04 | 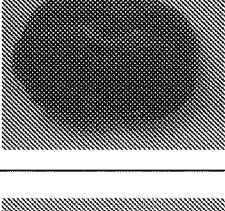 | 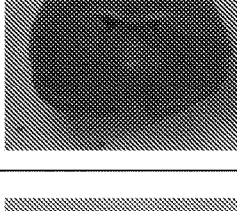 | 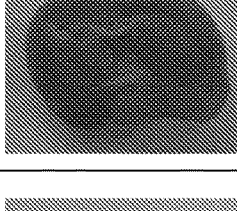 | 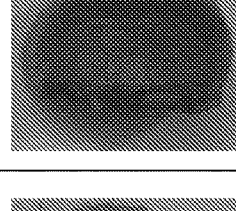 |
| RA05 | 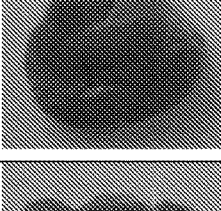 | 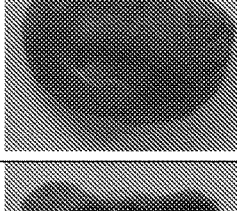 | 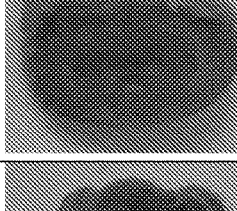 | 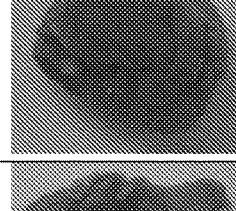 |
| RA06 | 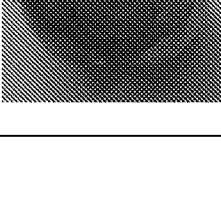 |  |  | 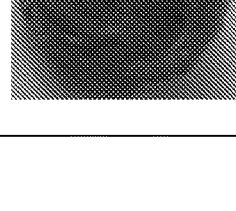 |

SYNERGISTIC BIOACTIVE COMPOSITIONS FOR TREATING NEUROLOGICAL DISORDERS

TECHNICAL FIELD OF THE INVENTION

The present invention relates to synergistic bioactive compositions for treating neurological disorders, preferably the composition is useful for treating ischemic brain damage. Particularly, the invention provides a synergistic, efficient, bioactive composition comprising specific combination of decarboxylated L-arginine called agmatine (AGM) and bio-optimized palmitoylethanolamide (PEA) and salts thereof along with pharmaceutically acceptable excipients or carriers.

More particularly, the invention relates to an anti-ischemic nutritional composition which is useful for treating cerebral ischemia, brain ischemia, cerebral infarction, cerebral stroke, neurotrauma, brain damage or brain injury.

BACKGROUND AND PRIOR ART

Neurological disorders are diseases of the brain, spine and the nerves that connect them, which include diseases like brain tumors, epilepsy, Parkinson's disease, stroke, dementia and like thereof.

Stroke is considered among the world's most debilitating disease with high mortality rate and it afflicts over 17 million people worldwide each year, of which more than 80% of cases are ischemic stroke. Stroke not only endangers the lives of victims but also burdens the families of the stroke survivors with significant caretaking and financial expenses.

Strokes are a heterogeneous group of disorders involving sudden interruption of cerebral blood flow that causes neurologic deficit. When a stroke occurs, a blood vessel in the brain gets blocked or bursts resulting in an irregularity in the oxygen supply to brain cells and therefore the brain cells begin to die. When brain cells die during a stroke; abilities controlled by that area of the brain such as memory and muscle control are lost. A stroke is a "brain attack" which can happen to anyone at any time.

Strokes are the second leading cause of death in the world, according to the American Stroke Association. Most strokes are caused by a blood clot, plaque buildup, blocked artery, leaking or bursting of a blood vessel or temporary disruption of blood flow to the brain.

During an ischemic stroke, the arteries supplying blood to the brain narrow or become blocked. These blockages are caused by blood clots or blood flow that's critically reduced. They can also be caused by pieces of plaque due to atherosclerosis breaking off and blocking a blood vessel.

There are two most common types of ischemic strokes—thrombotic and embolic. A thrombotic stroke happens when a blood clot forms in one of the arteries supplying blood to the brain. The clot passes through the bloodstream and becomes lodged, which blocks blood flow. An embolic stroke happens when a blood clot or other debris are formed in another part of the body and then travel to the brain.

According to the American Heart Association, ischemic stroke accounts for about 87 percent of all the strokes. The other type of stroke, known as a hemorrhagic stroke, happens when a blood vessel in or around the brain becomes weak and ruptures. Some people may experience only a temporary disruption of blood flow to the brain (transient ischemic attack, or TIA) that doesn't cause permanent damage.

Cerebral ischemia or brain ischemia is a condition that occurs when there isn't enough blood flow to the brain to meet metabolic demand. This leads to limited oxygen supply or cerebral hypoxia and leads to the death of brain tissue, cerebral infarction, or ischemic stroke. It is a sub-type of stroke along with subarachnoid hemorrhage and intracerebral hemorrhage.

There are two types of ischemia: focal ischemia which relates to a specific region of the brain and global ischemia which encompasses wide areas of the brain tissue.

Congenital heart defects and even sickle cell anemia have a higher tendency to develop cerebral ischemia in comparison to their healthy counterparts. A heart attack can also lead to cerebral ischemia due to the association that exists between heart attack and low blood pressure.

Cerebral ischemia results in generation of reactive oxygen species with neuronal necrosis, disruption of the blood-brain barrier (BBB), and release of proinflammatory cytokines particularly interleukin-1 beta (IL-1$\beta$) and tumor necrosis factor-alpha (TNF-$\alpha$).

Further cerebral ischemia occurs when blood flow to the brain is insufficient to meet metabolic demand. This can result from cerebral artery occlusion that interrupts blood flow, limits CNS supply of oxygen and glucose, and causes an infarction/ischemic stroke. Ischemia initiates a cascade of molecular events in neurons and cerebrovascular endothelial cells including energy depletion, dissipation of ion gradients, calcium overload, excitotoxicity, oxidative stress, and accumulation of ions and fluid. Blood-brain barrier (BBB) disruption is associated with cerebral ischemia and leads to vasogenic edema, a primary cause of stroke-associated mortality.

It is reported that the lack of blood flow results in severe damage (infarct) to the brain tissue. The infarcted tissue caused fluids to accumulate (edema) and results in swelling. The center of the brain is shifted to the right due to swelling from the left.

The excessive release of the excitatory neurotransmitter glutamate leads to the activation of postsynaptic glutamate receptors. The result is a massive increase in intracellular calcium concentration and unregulated activation of a number of processes that lead to neuronal death. This phenomenon is termed excitotoxicity.

The neurotoxicity of glutamate is the result of an excessive activation of the postsynaptic NMDA receptors, which start the massive inflow of ionic calcium, and of the AMPA receptors, which facilitate the incorporation of sodium into the cell. Both ions give rise to edema and neuronal necrosis.

Cerebral ischemia triggers a cascade of molecular interactions that result in a combination of cytotoxic and vasogenic edema, referred to as ischemic edema.

The most common cause of neurological deterioration and death during acute ischemic stroke is cerebral edema. It occurs in all ischemic strokes. Ischemic brain edema is initially cytotoxic because of disturbances in cell membrane. Later vasogenic edema sets in due to disruption of BBB.

Edema is frequently observed in ischemic stroke. Brain edema, defined as an abnormal increase in the brain water content, leads to an expansion of brain volume, and has a crucial impact on morbidity and mortality after stroke, in that it increases intracranial pressure, promotes cerebral herniations, and contributes to additional ischemic injuries [Klatzo, 1985, *Br J Anaesth* 57:18-22]. Edema causes mass-effect with distortion, tissue shift and increased intracranial pressure resulting in brain damage and death.

Ischemic brain edema is a combination of two major types of edema: cytotoxic (cellular) and vasogenic [Fishman R A.

*Cerebrospinal Fluid in Diseases in the Nervous System.* 2nd Ed. Philadelphia, PA: W.B. Saunders Co; 1992:103-155]. Cytotoxic edema, a consequence of neuronal swelling, occurs early during ischemia. At later stages, breakdown of the blood-brain barrier results in the development of vasogenic edema.

'Cytotoxic edema' is characterized by swelling of all the cellular elements of the brain. In the presence of acute cerebral ischemia, neurons, glia, astrocytes, and endothelial cells swell within minutes of hypoxia due to failure of ATP-dependent ion (sodium and calcium) transport. With the rapid accumulation of sodium within cells, water flows to maintain osmotic equilibrium. Increased intracellular calcium activates phospholipases and the release of arachidonic acid, leading to the release of oxygen-derived free radicals and infarction.

'Vasogenic edema' is characterized by an increase in extracellular fluid volume due to increased permeability of brain capillary endothelial cells to macromolecular serum proteins (e.g., albumin). Normally, the entry of plasma protein-containing fluid into the extracellular space is limited by tight endothelial cell junctions, but in the presence of massive injury, there is an increased permeability of brain capillary endothelial cells to large molecules.

It is further observed that damaged cells swell, injured blood vessels leak and blocked absorption pathways force fluid to enter the brain tissues. Cellular and blood vessel damage follows activation of an injury cascade. The cascade begins with glutamate release into the extracellular space. Calcium and sodium entry channels on cell membranes are opened by glutamate stimulation. Sodium builds up within the cell creating an osmotic gradient and increasing cell volume by entry of water. Increase in water causes dysfunction. Thus, hypoxia depletes the cells' energy stores disabling the sodium-potassium ATPase and reducing calcium exchange.

Calcium accumulates inside the cell activating intracellular cytotoxic processes. Microglial cells are activated and release free radicals and proteases which contribute to the attack on cell membranes and capillaries. Once the membranes are disrupted recovery of the cells is impossible [*Med J Armed Forces India.* 2003 October; 59(4): 326-331].

Therefore, the need arises to develop advanced therapy that limits or regulates blood-brain barrier (BBB) permeability along with inhibition of cytotoxins and free radicals release.

There are different therapies available in the art to control brain stroke. If a stroke is caused by a blood clot, the patient may be able to receive a clot-busting drug such as tissue plasminogen activator (t-PA) to dissolve the clot and help restore blood flow to the damaged area of the brain. Medications to dissolve blood clots or blood-thinning drugs such as aspirin or warfarin, heparin or clopidogrel are also prescribed for treating ischemic stroke.

Other stroke treatments include surgery to remove blood from around the brain and repair damaged blood vessels.

Post-stroke treatment may also include efforts to prevent another stroke by controlling or eliminating risk factors such as high blood pressure, high cholesterol and diabetes.

Further WO1996022104A1 (Maas BioLAB LLC) discloses use of cyclosporin A for nervous insult treatment. WO2015138974A1 relates to combined administration of thrombolytic agent tPA and Anti-VEGF treatment for cerebral ischemia. Tissue plasminogen activator (tPA) is given via intravenous therapy (IV) and works by dissolving the clot and improving blood flow to the part of the brain being deprived of blood flow.

Additionally, U.S. Pat. No. 7,635,691B2 discloses the role of free CDP-Choline for treating cerebral ischemia.

Neuroprotective effect and proposed mechanism of different drugs such as calcium channel blockers-nimodipine and nifedipine mebudipine cinepazide maleate; anti-coagulants-heparin; opiates-nalaxone; tetracycline antibiotic-minocycline; brain natural histidine, dipeptide, antioxidants suffer from limited efficacy, costly treatment with side effects.

Thus, there is a need for non-toxic, cost-effective, safe bioactive compounds, which can give significant neuroprotective treatment without any side effects.

NeuroAiD™ herbal composition is a medicine indicated for post-stroke rehabilitation. It triggers the production of new neurons in the brain (neurogenesis) and favors connections between neurons by stimulating the formation of new dendrites and synapses (neuroplasticity). However, the multiple ingredients dietary composition is not feasible to give desired site specific action.

Intriguingly, it is found that natural metabolite of the amino acid like L-arginine called agmatine, which is formed when arginine is decarboxylated by the enzyme arginine decarboxylase is useful for treating several indications such as cardio protection, diabetes, decreased kidney function, neuroprotection (stroke, severe CNS injuries, epilepsy, glaucoma, and neuropathic pain), and psychiatric conditions (depression, anxiety, schizophrenia, and cognition).

WO2001095897A1 discloses use of agmatine, congeners, analogs or derivatives thereof for preventing or treating epilepsy, seizures and other electroconvulsive disorders.

Further, WO200819594A1 discloses agmatine sulfate dihydrate composition useful for treating drug abuse, anti-inflammatory, lowering blood glucose levels.

US20150005387A1 discloses compositions containing agmatine for the treatment of pathologies associated with cellular hyperproliferation, particularly in the treatment of cancer.

Additionally, the cognitive effect of agmatine is also reported in some prior art; U.S. Pat. No. 9,993,447B2 discloses agmatine salt formulation for improving athletic performance, training resistance and/or cognitive function.

U.S. Pat. No. 6,150,419 indicates that agmatine exerts anti-allodynic effect by acting as NMDA receptor antagonism.

The agmatine may serve as a precursor for biosynthesis of polyamines compounds that possess a wide range of activities both within and external to the central nervous system (e.g., modulation of postsynaptic receptors, such as N-methyl-D-aspartate (NMDA), nicotinic and benzodiazepine receptors, antiplatelet, anti-inflammatory and anticoagulant activities). The effect of the polyamines spermine, spermidine and putrescine in protecting against ischemia-induced nerve cell death in gerbils were described by Gilad G. M. et al. in *Life Sci* (1989) 44:1963-1969; *Exp Neurol* (1991) 111:349-355.

Further U.S. Pat. No. 5,677,349A Gilad et al. discloses methods for treating neurotrauma or neurodegenerative disease in a human by administering agmatine (4-aminobutylguanidine), wherein agmatine modulates several neurotransmitters such as nicotine, glutamate (NMDA), and adrenaline and regulates nitric oxide (NO) production.

Although substantial research is available for agmatine or salts thereof, the role of agmatine to control ischemic brain edema and neuroinflammation to give better result in post stroke recovery or cerebral ischemia is not substantially demonstrated or reported.

It is observed that influx of inflammatory cells such as leukocytes into the ischemic territory results in substantial collateral damage. Activation of astrocytes and microglia, together with the release of cytokines, augments the inflammation. The inherent therapeutic activity of agmatine has limited anti-inflammatory function, which is not enough to control neuroinflammation observed during traumatic brain injury or cerebral ischemia.

Therefore, the need arises to add efficient, non-toxic, anti-inflammatory agent to enhance the activity of nutritional composition by stabilizing activation of non-neuronal cells and neuronal sensitization thereof.

The inventors of the present invention have developed efficient, non-toxic, cost effective and environmentally feasible and safe synergistic composition based on combination or concomitant or hybrid neuroprotective therapy by incorporating bioactive neuroprotective agents in specific amount that act in dual mechanism.

Particularly, the inventors have formulated synergistic combination of agmatine and fatty amino acid called palmitoylethanolamide for lowering the risk of brain damage or improving function in ischemia-reperfusion, brain injury-related disorders.

OBJECT OF THE INVENTION

The primary object of the invention is to provide a synergistic bioactive composition for treating neurological disorders.

Another object of the invention is to provide a synergistic composition of bioactive agents for treating cerebral injury.

Particularly, the object of the invention is to provide an anti-ischemic nutritional composition with improved therapeutic activity.

Further object of the invention is to provide a synergistic combination of therapeutically active, natural, non toxic, safe ingredients for treating cerebral ischemia, or cerebrovascular ischemia.

A preferred object of the invention is to provide a synergistic combination of therapeutically active, biologically significant decarboxylated alpha amino acid and fatty acid amine compounds along with pharmaceutically acceptable carriers for treating post-stroke brain damage or ischemic stroke.

Another object of the invention is to provide a bioactive composition with synergistic effect for treating cerebral ischemia by attenuating ischemic brain edema simultaneously or concomitantly controlling pain sensitivity Another object of the invention is to provide a synergistic therapeutically active remedy for treating cerebral ischemia through site specific action with no adverse effects.

SUMMARY OF THE INVENTION

To meet the above objects, the inventors of the present invention carried out thorough experiments to establish therapeutic effects of the bioactive ingredients or nutrients or natural substances present in the composition that ameliorate blood-brain barrier (BBB) permeability and neuroinflammation in a subject suffering from neurological diseases like traumatic brain injury or stroke or brain damage.

In an aspect, the invention relates to synergistic bioactive compositions comprising therapeutically active nutrients along with pharmaceutically acceptable carriers for treating cerebral ischemia or related conditions.

In another aspect, the invention provides a hybrid neuroprotective therapy, which comprises synergistic combination of decarboxylated alpha-amino acid i.e., (L-arginine) and palmitoylethanolamide (PEA) along with pharmaceutically acceptable excipients.

In another particular aspect, the present invention provides synergistic nutritional compositions for improving cerebral ischemia-induced diseases or conditions comprising specific combination of agmatine (AGM) and palmitoylethanolamide (PEA) and/or salts thereof along with pharmaceutically acceptable excipients.

In preferred aspect, the present invention provides synergistic nutritional composition, wherein the bioactive moieties are present in specific amount, where it acts synergistically in the treatment of brain ischemia or stroke. Accordingly, AGM attenuates brain infarct and edema volume by limiting blood brain barrier disruption and protects against cell damage induced by NMDA and glutamate; concomitantly PEA targets neuroinflammation by modulating the activation of non-neuronal cells and controlling neuronal sensitization. This synergistic neuroprotective effect can also be effective for relieving central and/or peripheral neuropathic pain.

In yet another aspect, the invention provides a method for the prevention or treatment of cerebral ischemia induced diseases or conditions, in particular reducing infarct size, relieving brain water edema, neuroinflammation, improving the neurological symptoms and cognitive dysfunction, wherein the method comprises administration of synergistic composition comprising therapeutically effective amount of agmatine and PEA to a subject in need thereof.

In one more aspect, the invention provides combination of naturally occurring nutrients for improving neurological disorders without any adverse effect, wherein the combination comprising therapeutically effective amount of AGM or pharmaceutically acceptable salts thereof are co-administered with micronized bioavailable form of PEA, optionally in presence of bioenhancer.

In another aspect, the invention provides cost effective, non-toxic, efficient and environmentally safe composition with synergistic effect of bioactive to control cerebral ischemia induced diseases or conditions without any adverse effect.

In yet another aspect, the invention relates to synergistic nutritional compositions comprising combination of AGM or salts thereof present in the range of 1-2000 mg; and PEA present in the range of 1-3000 mg; along with pharmaceutically acceptable excipients/carriers optionally in presence of bioenhancer.

In one more aspect, the invention discloses synergistic nutritional composition which is useful for treating neurological disorders; moreover the composition is effective for treating cerebral ischemia, brain ischemia, cerebral infarction, cerebral stroke, cerebral edema, postischemic stroke, acute ischemic stroke, hemorrhagic stroke, transient ischemic attacks, neurodegenerative diseases, hypoxic brain injury brain trauma, nervous system trauma or conditions related to neuroplasticity, neuroinflammation, brain attack, brain damage, cerebrovascular accident, cognitive dysfunction and central or peripheral neuropathic pain and likewise cerebrovascular disorders.

ABBREVIATIONS

AGM: Agmatine
PEA: Palmitoylethanolamide
NMDA: N-methyl-D-aspartate
BBB: Blood Brain Barrier
CNS: Central nervous system TNF-alpha: Tumour Necrosis Factor alpha IL-6: Interleukin 6

BRIEF DESCRIPTION OF FIGURES

FIG. 3 illustrates the effect of test substances on Rat TTC staining—Group 1—Normal Control [RA-01 to RA-06 represent Rat model];

FIG. 4 illustrates the effect of test substances on Rat TTC staining—Group 2—Positive Control;

FIG. 5 illustrates the effect of test substances on Rat TTC staining—Group 3—Standard Cerebroprotein hydrolysate (Tablet);

FIG. 6 illustrates the effect of test substances on Rat TTC staining—Group 4—(Agmatine Sulphate—AGM);

FIG. 7 illustrates the effect of test substances on Rat TTC staining—Group 5—(Bio-Optimized Palmitoylethanolamide—PEA);

FIG. 8 illustrates the effect of test substances on Rat TTC staining—Group 6—(combination AGM+Bio-optimized PEA).

DETAILED DESCRIPTION OF THE INVENTION

Figure 1:
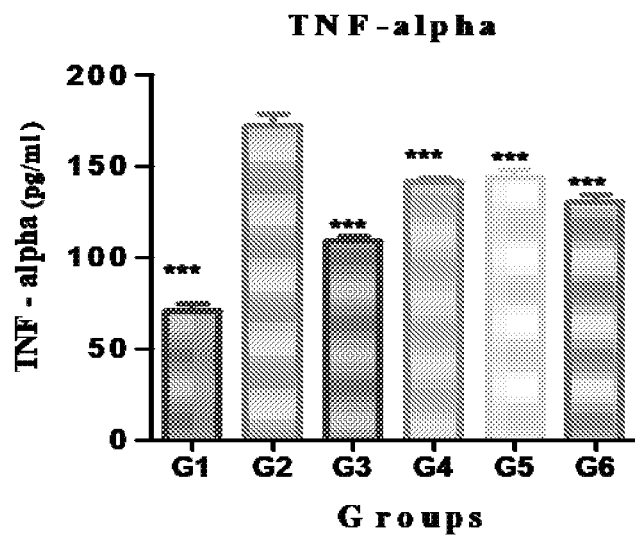
FIG. 1 illustrates the effect of test substances on Rat TNF alpha levels.

The invention will now be described in detail in connection with certain preferred and optional embodiments, so that various aspects thereof may be more fully interpreted and comprehended. However, any skilled person in the art or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the art.

The singular forms "a," "an," and "the" include plural reference unless the context clearly dictates otherwise. Also, the term 'composition' does not limit the scope of the invention, for it may include multiple compositions that can be illustrated to establish best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, alkali or alkaline earth metal salts, as well as solvates, co-crystals, polymorphs, isomers, enantiomers, congeners and the like of the salts.

Furthermore, the compounds or active ingredients of the present invention can exist in particular geometric isomeric or enantiomeric, enantiomeric excess or diastereomeric, diastereomeric excess or stereoisomeric forms. The invention contemplates all such compounds, including dextrorotatory and levorotatory (DL) isomers, rectus and sinister (RS) configuration, cis and trans configurations, optically active isomers (dl). All such isomers as well as racemic mixtures thereof are intended to be included in this invention.

In a preferred embodiment, the invention relates to nutritional compositions comprising synergistic combination of a biologically active decarboxylated alpha amino acid compound and a fatty acid amide, optionally in presence of a bioenhancer along with pharmaceutically acceptable excipients or carriers; wherein the decarboxylated alpha amino acid compound is decarboxylated L-arginine called agmatine (AGM) and the fatty acid amide compound is palmitoylethanolamide (PEA) and/or salts thereof.

In another preferred embodiment, the invention provides synergistic nutritional compositions comprising specific combination of bioactive moieties namely agmatine (AGM) and palmitoylethanolamide (PEA) along with pharmaceutically acceptable excipients.

According to the invention, the decarboxylated alpha L-arginine compound i.e., agmatine reduces brain edema volume by limiting BBB disruption.

The agmatine is an amine, synthesized by decarboxylation of L-arginine by arginine decarboxylase (ADC).

It is a decarboxylated form of L-Arginine which is chemically known as 1-Amino-4-guanidinobutane; 4-(Aminobutyl) guanidine; N-4-Aminobutylguanidine.

The agmatine is present in small amounts in plant, animal, and fish-derived foodstuff and gut microbial production is an added source for agmatine. It is a natural metabolite of the amino acid L-arginine which is found naturally in ragweed pollen, ergot fungi, octopus muscle, herring sperm, sponges, and the mammalian brain. A high agmatine level was found in the healthy sprouts and flower buds of broccoli and cauliflower flower buds, soybean sprouts, radish and flaxseed sprouts, corn grain, lentils.

In another embodiment, the invention provides synergistic composition of biologically or therapeutically active nutrients, wherein the amino acid based active moiety is Agmatine. It attenuates brain edema by limiting BBB disruption and blocking the accumulation of brain water content after cerebral ischemia. Agmatine significantly reduces infarct volume and brain swelling after ischemic injury. The agmatine controls permeability of the blood brain barrier thus the entry of plasma protein-containing fluid or macromolecules into the brain capillary endothelial cells is protected after brain injury or stroke.

In another embodiment, the invention discloses that agmatine acts as NMDA receptors antagonist to rescue ischemic brain injury with no side effects. Agmatine prevents hippocampal neurons from excitatory cell damage, by blocking NMDA receptor channels. Agmatine binds to 2 sites of the NMDA (N-methyl-D-aspartate) receptor and prevents glutamate from binding to them. This prevents neuron death from overexcitation due to the neurotransmitter glutamate. It will improve cognitive function after brain injury or stroke.

The neuroprotection of agmatine against NMDA/glutamate induced excitotoxic insults shows significant implications for recovering brain injury.

Further, the agmatine plays an essential role as a neurotransmitter or neuromodulator in the brain.

In another embodiment, the invention relates to agmatine salts, wherein the salts are hydrosoluble stable organic or inorganic salts of agmatine. Preferably the salts are selected from pharmaceutically acceptable salts including but are not limited to, agmatine sulphate, agmatine orotate, agmatine di-hydrochloride, agmatine phosphate and like thereof.

In another embodiment, the invention provides synergistic nutritional compositions comprising agmatine and salts thereof, wherein the preferable salt is sulfate having molecular formula $C_5H_{16}N_4O_4S$, represented by Formula-I

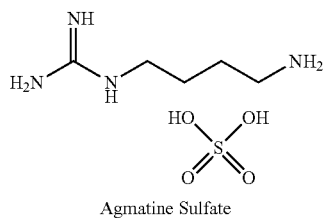

Agmatine Sulfate

The agmatine sulfate is also known as 1-(4-Aminobutyl) guanidine sulfate; 1-Amino-4-guanidinobutane sulfate salt.

In another embodiment, the invention provides synergistic nutritional composition comprising therapeutically effective amount of AGM alone or salts thereof, wherein the AGM salt, particularly AGM sulfate is present in the range of 1-2000 mg of total composition.

In yet another embodiment, the invention provides a hybrid or concomitant or combination therapy for treating cerebral ischemic conditions, wherein the other active moiety is PEA that gives synergistic effect to the composition to control neuroinflammation or nerve sensitivity.

PEA, an endogenous fatty acid amide, is a congener of the endocannabinoid anandamide (N-arachidonoylethanolamine or AEA) that belongs to a class of lipid mediators, the superfamily of N-acylethanolamine (NAE) endogenous biologically active lipids including the endogenous cannabinoid receptor ligand anandamide and the satiety factor oleoylethanolamine. It is a weak ligand of the cannabinoid 1 ($CB_1$) and cannabinoid 2 ($CB_2$) receptors.

PEA is a natural compound, and found in a variety of food products, such as soybean, lecithin, egg yolk, and peanut meal.

It is represented by chemical formula $C_{18}H_{37}NO_2$ as depicted in Formula-II

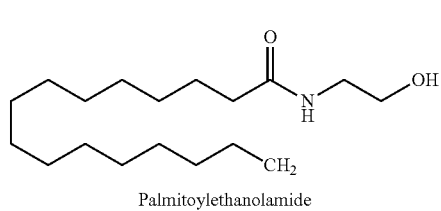

Palmitoylethanolamide

Palmitoylethanolamide (PEA), is an N-(long-chain-acyl) ethanolamine that is the ethanolamide of palmitic (hexadecanoic) acid. Further palmitoylethanolamide (PEA) can also be referred as 'Hydroxyethylpalmitamide', 'Palmidrol', 'N-Palmitoylethanolamine', 'Palmitylethanolamide'.

Due to lipophilic nature and large particle size in the native state, molecules of PEA have limitations in terms of solubility and bioavailability. The micronization technique is frequently used in the pharmaceutical field to enhance the dissolution rate of drug and thereby reduce variability of drug absorption when orally administered.

In another embodiment, the palmitoylethanolamide (PEA) can be used in various forms including but not limited to non-micronized form (nm-PEA), micronized form (m-PEA), or ultra-micronized form (um-PEA).

In another embodiment, the composition comprises micronized palmitoylethanolamide (m-PEA) having particle size in the range of 2 μm-10 μm, preferably in the range of 2 μm-6 μm.

In another embodiment, the PEA used in the composition is present in the combination of suitable solubilizer or bioenhancer to enhance the solubility and bioavailability of poorly water soluble PEA, the efficacy of micronized PEA is improved under optimum condition by using bioenhancer that is collectively termed as Bio-optimized PEA.

The active ingredient PEA is in micronized form where pharmaceutically acceptable solubilizers and bioenhancers are added under optimized conditions to get PEA with improved bioavailability and efficacy.

In an additional embodiment, the micronized PEA can be incorporated in micelles, encapsulation or complex.

It is observed that palmitoylethanolamide, when administered in an appropriate form e.g., micronized and/or ultra micronized gives significant results.

The inventors observed that acute CNS injuries, such as stroke or trauma result in a prolonged inflammatory response involving microglial activation and infiltration of macrophages and neutrophils, which has the potential to cause secondary injury.

Additionally, the inflammation in the CNS is driven by the activation of resident microglia, astrocytes and infiltrating peripheral macrophages, which release excessive anti- and pro-inflammatory cytokines, chemokines, neurotransmitters and reactive oxygen species. This inflammatory state inadvertently causes further damage to neurons and produces detrimental conditions for neurogenesis.

In another embodiment, the bioactive compound PEA exerts neuroprotection and reduces inflammatory secondary events associated with brain ischemia reperfusion injury (middle cerebral artery occlusion (MCAO)). PEA significantly inhibits the inflammatory cascade of blood-borne neutrophil and phagocyte infiltration in ischemia.

It further mediates neuroinflammation propagation by increasing microglial cell motility.

Mast cells are early responders in the regulation of acute BBB changes after cerebral ischemia. According to the invention the effective dose of PEA controls mast cell activation which limits hypoxic-ischemic brain damage.

In a further embodiment, the invention provides synergistic nutritional composition comprising therapeutically effective amount of PEA along with pharmaceutically acceptable salts thereof, wherein PEA is present in a range of 1-3000 mg of total composition, preferably in a range of 1-500 mg of total composition.

Notably, the present composition exhibits therapeutic potential in treatment of brain edema after brain injury, such as stroke and brain trauma, wherein the AGM attenuates brain infarct and edema volume by limiting blood brain barrier disruption and protects against cell damage induced by NMDA and glutamate; concomitantly PEA targets neuroinflammation by modulating the activation of non-neuronal cells and controlling neuronal sensitization; PEA further enhances neurogenesis after brain ischemia. This synergistic neuroprotective effect can also be effective for relieving central and/or peripheral neuropathic pain.

More particularly, the present invention offers synergistic cerebroprotective effects of combined agmatine sulfate and bio-optimized palmitoylethanolamide for treating cerebral ischemia/reperfusion injury. The active moieties of the present composition are present in a therapeutically effective amount. The composition imparts significant neuroprotective effect to the subject in need thereof with enhanced bioavailability and efficacy.

In one embodiment, the invention provides a synergistic nutritional composition(s) for treating neurological disorders in a subject in need thereof comprising a therapeutically active exogenous combination of a crystalline form of decarboxylated L-arginine and a bio-optimized palmitoylethanolamide and salts thereof, wherein the crystalline form of the decarboxylated L-arginine and the bio-optimized palmitoylethanolamide are present in a weight ratio of 1:0.1 to 1:5 along with pharmaceutically acceptable excipients.

In one preferred embodiment, the invention provides synergistic nutritional compositions for treating ischemic brain damage comprising therapeutically active exogenous combination of crystalline decarboxylated L-arginine and bio-optimized palmitoylethanolamide and salts thereof which are present in the weight ratio of 1:0.1 to 1:5 along with pharmaceutically acceptable excipients.

In another preferred embodiment, the invention provides synergistic nutritional compositions for treating ischemic brain damage comprising therapeutically active exogenous combination of crystalline decarboxylated L-arginine and bio-optimized palmitoylethanolamide (PEA) and salts thereof which are present in the weight ratio of 1:0.1 to 1:2.5 along with pharmaceutically acceptable excipients.

In yet another embodiment, the invention provides synergistic combination wherein the decarboxylated L-arginine salt is agmatine sulfate which is present in crystalline form with organoleptic properties.

The term 'organoleptic' pertains to the analysis of the properties of products and materials mainly foodstuffs by means of the sense organs. Organoleptic testing is usually done by tasters. It is property of the substances that create an individual experience via the senses including taste, sight, smell, and touch.

In yet another preferred embodiment, the invention discloses potent anti-ischemic synergistic nutritional composition comprising therapeutically active exogenous blend of crystalline form of organoleptic agmatine sulphate (AGM) and bio-optimized palmitoylethanolamide (PEA), wherein AGM sulfate and bio-optimized PEA are present in a weight ratio of 1:0.1 to 1:5; preferably in a weight ratio of 1:0.1 to 1:2.5 along with pharmaceutically acceptable excipients.

In one more embodiment, the invention provides synergistic nutritional composition comprising crystalline form of decarboxylated L-arginine, which is present in a range of 40% to 80% by weight of the total composition.

In a further embodiment, the invention provides the anti-ischemic synergistic nutritional composition comprising white crystalline powder of organoleptic agmatine sulphate, which is present in a range of 40% to 75% by weight of the total composition.

In yet another embodiment, the invention provides synergistic nutritional composition comprising micronized, bioavailable and soluble form of PEA, which is present in a range of 25% to 60% by weight of the total composition.

In another embodiment, the invention provides anti-ischemic synergistic nutritional compositions, wherein the effective amount of bio-optimized palmitoylethanolamide is present in a range of 25% to 60% by weight of the total composition.

In another embodiment, the present invention provides the synergistic effect for treating cerebral ischemia, wherein the effective amount of AGM attenuates brain edema, cerebral infarction and intracranial pressure by regulating blood brain barrier permeability; on the other side the anti-inflammatory bioactive called PEA efficiently mitigates neuroinflammation and enhances neurogenesis.

In yet another embodiment, the present composition is also useful for treating cerebral ischemia-induced neuropathic pain either central or peripheral or both through synergistic pathways.

In the present invention, the term 'hybrid (neuro)protective therapy' or 'combination therapy' or 'concomitant therapy' denotes the characteristics or inventive feature of the present composition, wherein the two active moieties performing simultaneous function in systematic pathways without any deviation or overlapping of the mechanism, consequently improve the cerebral ischemic induced conditions In an additional embodiment, the invention provides additional bioenhancer to improve the bioavailability of the present composition where it enhances the absorption of active ingredients inside the body.

In another embodiment, the invention provides the anti-ischemic synergistic nutritional composition for treating ischemic neuronal damage, neuronal ischemic injury, ischemic cell death in brain neurons, ischemic cerebral damage, brain Ischemia.

Notably the significance of the present compositions is evaluated by known techniques like histopathological techniques including TTC staining and by evaluating biochemical parameters like Inflammatory markers—TNF-alpha and IL-6.

In another embodiment, the invention provides synergistic bioactive composition which is useful for treating cerebral ischemia, brain ischemia, cerebral infarction, cerebral stroke, postischemic stroke, acute ischemic stroke, hemorrhagic stroke, transient ischemic attacks, neurodegenerative diseases, hypoxic brain injury brain trauma, nervous system trauma or conditions related to neuroplasticity, neuroinflammation, brain attack, brain damage, cerebrovascular accident or disorders, cognitive dysfunction and central or peripheral neuropathic pain.

In another embodiment, the invention provides the synergistic nutritional compositions for treating neurological disorders in a subject (human) in need thereof comprises oral administration of therapeutically effective amount of said synergistic nutritional compositions, wherein the neurological disorders are selected from the group consisting cerebral ischemia, cerebral infarction, cerebral stroke, cerebral edema, postischemic stroke, acute ischemic stroke, hemorrhagic stroke, transient ischemic attacks, hypoxic brain injury, brain trauma, nervous system trauma or conditions related to neuroplasticity, neuroinflammation, brain attack, brain damage, cerebrovascular accident, cognitive dysfunction.

As used herein, the term "therapeutically effective amount" is intended to mean the amount of active compound of the present invention that is effective for treating cerebral ischemia induced diseases or conditions or pain through synergistic effect.

As used herein, the term "pharmaceutically acceptable carriers, diluents or excipients" is intended to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethyleneglycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration.

In the context of the present invention, the terms "treatment" and the like refer to alleviate, mitigate, prophylaxis, attenuate, manage, regulate, modulate, control, moderate, prevent, inhibit, stabilize or cure the pre-existing or occurrence of neurological disorders like stroke conditions.

The present composition is used for reducing brain edema volume and inflammation in the subject in need thereof, means either the administration of the remedy to prevent occurrence or pre-existing cause of neurological disorders.

The 'subject in need thereof' pertains to a subject preferably mammal, more preferably a human sustaining pre-existing or onset symptoms of stroke or ischemia, brain damage or injury.

Interestingly, the present synergistic composition is non-hazardous, non-toxic and safe for human consumption without any side effects, therefore the instant composition can also be administered under preventive therapy for healthy subjects.

The therapeutically effective amount of such actives will vary depending upon the subject and disease condition being treated, the weight and age of the subject, the severity of the disease condition, the manner of administration and the like, which can readily be determined by one of ordinary skill in the art.

Thus, a "therapeutically effective" amount is an amount that reduces the risk, potential, possibility or occurrence of a disease or disorder, or provides advanced alleviation, mitigation, and/or reduction or restoration of at least one indicator/biomarker (e.g., blood or serum CRP level), and/or decrease in at least one clinical symptom of neurological disorders (e.g. cerebral ischemia, stroke).

In another embodiment, the invention relates to a synergistic composition prepared in a manner well known in the pharmaceutical art, and administered by a variety of routes, depending upon whether local or systemic treatment is desired and upon the area to be treated. The preferable route of administration includes but is not limited to sublingual, rectal, topical, parenteral, nasal or oral.

Therapeutic (prescription) supplements are generally administered by the oral or parenteral or nasal routes for curing stroke conditions. The therapeutic administration of compositions of the present invention may be in conjunction with other therapies.

Further, the present synergistic nutritional composition is administered to a subject in a form suitable for oral use, such as a tablet, capsule (in the form of delayed release, extended release, sustained release, enteric coated release); hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup. In another embodiment, the composition is formulated for parenteral use including intravenous, subcutaneous, intramuscular, intravascular, infusion, intraperitoneal, or intradermal routes of administration.

In another embodiment, the oral administration of an effective dose of the present synergistic nutritional composition comprising exogenous blend of AGM and PEA in specific weight ratio of 1:0.6 significantly improves cognitive function.

In some embodiment, the pharmaceutically acceptable carriers, diluents or excipients are selected from the group consisting of adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposomes and cyclodextrins, encapsulating polymeric delivery systems or polyethyleneglycol matrix, which is acceptable for use in the subject, preferably humans. Excipients may also include, for example: antiadherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, additives, or waters of hydration.

In some embodiment of the invention, the diluents are selected from starches, hydrolyzed starches, partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, β-cyclodextrin, dextrates, dextrose, erythritol, ethylcellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the amount of diluent in the composition/formulation is present in the range of 1% to 40% by weight of the total composition/formulation.

In some embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethylcellulose, guar gum, hydrogenated vegetable oil, mineral oil, hydroxyethyl cellulose, hydroxymethyl cellulose hydroxyl ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax.

In some embodiment of the invention, the amount of binder in the composition/formulation is present in the range of 0.1 to 40% by weight of the composition/formulation.

In further embodiment, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium, or sodium benzoate or the like.

In some embodiment of the invention, the amount of lubricant in the composition/formulation is present in the range of 0.1% by wt. to 5.0% by weight of the total composition/formulation.

In another embodiment, the solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In one embodiment, the amount of solubilizing agent or surfactant in the composition/formulation of the present invention ranges from 0.1% to 10%, preferably 0.1% to 5.0% by weight of the composition/formulation.

In some embodiment, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In some embodiment of the invention, the amount of glidant present in the composition/formulation ranges from 0.1% to 5.0% by weight of the total composition/formulation.

In some embodiment of the inventions, the stabilizers are selected from the group consisting of alginate, agar, carrageen, gelatin, guar gum, gum arabic, locust bean gum, pectin, starch, xanthan gum, trehalose and likewise.

In some embodiment of the invention, the amount of stabilizers in the composition/formulation range from 0.1% to 10.0% by weight of the total composition/formulation.

In some embodiment, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In some embodiment of the invention, the amount of solvent in the composition/formulation is used in a quantity sufficient to make the weight of the composition/formulation 100%.

The additional additives include polymer, a plasticizer, a sweetener, and a powdered flavor, preservative, colorant, surfactant and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used. The additives are used in the range of 1 to 30% w/w of unit dose.

In another embodiment, the invention provides synergistic nutritional composition comprising exogenous blend of AGM and Bio-optimized PEA along with pharmaceutical excipients, wherein pharmaceutical excipients are a diluent present in the range of 1 to 30%; a binder present in the range of 0.1 to 30%; a lubricant present in the range of 0.1 to 5.0%; a glidant present in the range of 0.1 to 5.0%; an additive present in the range of 1 to 10%; a surfactant present in the range of 0.1 to 5.0%; a stabilizer present in the range of 0.1 to 10.0%, by weight of total composition.

In another embodiment, the invention provides synergistic nutritional composition comprising exogenous blend of AGM and Bio-optimized PEA along with pharmaceutical excipients, wherein pharmaceutical excipients are diluent present in the range of 1 to 25%; binder present in the range of 0.1 to 20%; lubricant present in the range of 0.1 to 5.0%; glidant present in the range of 0.1 to 3.0%; additive present in the range of 1 to 5%; surfactant present in the range of 0.1 to 3.0%; stabilizer present in the range of 0.1 to 5.0%, by weight of total composition.

Advantageously, the present synergistic nutritional composition is non-hazardous, non-toxic and safe for human consumption without any severe side effects, therefore the present composition can also be used as preventive therapy in healthy subjects.

In a preferred embodiment, the present medicinal composition/formulation is formulated for oral administration. Specifically, the solid medicinal compositions, for example, can be in the form of tablets, capsules, pills, hard capsules filled with liquids or solids, soft capsules, sachets, powders, granules, suspensions, solutions or modified release formulations. Further oral agmatine is absorbed from the gastrointestinal tract and readily distributed throughout the body.

Formulations of the present invention suitable for oral administration can be presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

Further, the present composition can be formulated in the form of age-appropriate pediatric oral dosage forms such as syrup, minitablets, chewable formulations, orodispersible films orodispersible tablets.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day, preferably about 100 mg per day to about 1500 mg per day.

In some embodiment, the total daily dose can be administered orally in the range of about 5 mg to about 2000 mg per day, and preferably about 10 mg to about 1000 mg per day.

The synergistic nutritional compositions, comprising specific combination of decarboxylated L-arginine called agmatine (AGM) and bio-optimized palmitoylethanolamide (PEA) and salts thereof along with pharmaceutically acceptable excipients or carriers, wherein the effective unit dose for oral administration is formulated in the range of 250 to 1000 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art.

Further, it is noted that the dietician or nutritionist or certified physician knows how and when to interrupt, adjust or terminate therapy in conjunction with an individual patient's response.

The use of any and all examples, or exemplary language (e.g., "such as") provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway.

This invention may be embodied in other forms or carried out in other ways without departing from the spirit or essential characteristics thereof. The present disclosure is therefore to be considered as in all respects illustrative and not restrictive, the scope of the invention being indicated by the appended claims and examples, and all changes or alterations which come within the ambit of equivalency are intended to be encompassed therein.

EXAMPLES

Example-1 i. Composition 1: Synergistic Blend

| Ingredients | w/w % |
| --- | --- |
| Agmatine Sulfate (Decarboxylated L-arginine) | 40%-80% |
| Bio-Optimized Palmitoylethanolamide (PEA) | 25%-60% | ii. Composition 2: Tablet/Capsule

| Ingredients | w/w % unit dose |
| --- | --- |
| Agmatine Sulfate | 60 ± 5% |
| Bio-Optimized PEA | 35 ± 5% |
| Excipient | 5-10% |
| Average Weight (%) | 100% |
| Average weight in mg | 800-900 mg | iii. Composition 3: Tablet/Capsule

| Ingredients | w/w % unit dose |
| --- | --- |
| Agmatine Sulfate | 55 ± 8% |
| Bio-Optimized PEA | 35 ± 8% |
| Excipient | 10-20% |
| Average Weight (%) | 100% |
| Average weight in mg | 400-500 mg | iv. Composition 4: Tablet/Capsule

| Ingredients | w/w % unit dose |
| --- | --- |
| Agmatine Sulfate | 62.5% |
| Bio-Optimized PEA | 37.5% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | v. Composition 5: Tablet/Capsule

| Ingredients | w/w % unit dose |
| --- | --- |
| Agmatine Sulfate | 50% |
| Bio-Optimized PEA | 30% |
| Diluent | 1-20% |
| Binder | 0.5-5% |
| Glidant | 0.5-5% |
| Lubricants | 0.5-5% |
| Additives | 1-10% |
| Solvent | QS | vi. Composition 6: Tablet/Capsule

| Ingredients | mg per unit dose |
| --- | --- |
| Agmatine Sulfate | 500 |
| Bio-Optimized PEA | 300 |
| Microcrystalline Cellulose | 1-20 |
| Silicon dioxide | 2-15 |
| Hydroxypropyl Methylcellulose | 1-10 |
| Zinc Stearate | 1-10 |
| PVP K-30 | 5-10 |
| Talc | 1-10 |
| Polysorbate 80 | 1-10 |
| Manitol | 1-20 |
| Propylene Glycol | QS |
| Water | QS |
| Average weight in mg | 800-900 mg | vii. Composition 7: Tablet/Capsule

| Ingredients | mg per unit dose |
| --- | --- |
| Agmatine Sulfate | 500 |
| Bio-Optimized PEA | 300 |
| Sodium ascorbate | 1-10 |

-continued

| Ingredients | mg per unit dose |
|---|---|
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Manitol | 5-20 |
| Alcohol | QS |
| Water | QS |
| Average weight in mg | 500-580 mg | viii. Composition 8: Tablet/Capsule

| Ingredients | mg per unit dose |
|---|---|
| Agmatine Sulfate | 500 |
| Bio-Optimized PEA | 300 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Manitol | 5-20 |
| Methylene Chloride | QS |
| Water | QS |
| Average weight in mg | 800-900 mg | ix. Composition 9: Tablet/Capsule

| Ingredients | mg per unit dose |
|---|---|
| Agmatine Sulfate | 250 |
| Bio-Optimized PEA | 150 |
| Ascorbic acid | 1-10 |
| Microcrystalline Cellulose | 1-10 |
| Silicon dioxide | 1-10 |
| Hydroxypropyl Methylcellulose | 1-10 |
| Magnesium Stearate | 2-10 |
| PVP K-30 | 5-10 |
| Talc | 1-10 |
| Polysorbate 80 | 5-20 |
| Manitol | 5-20 |
| IPA | QS |
| Water | QS |
| Average weight in mg | 400-500 mg |

Example 2: Animal Study

"Neuroprotective Effect of Test Product against Global Ischemia Reperfusion Induced Brain Injury (Cerebral Infarction) in Wistar Rats"

Test System and Animal Husbandry
  Species: Rats
  Strain: Wistar
  Sex: Male
  No. of animals: 36 Animals (n=6 per group)
  Body weight: 200-220 gm
  CPCSEA Registration Number-1803/PO/RcBi/S/2015/CPCSEA
Animal House Conditions
  Lighting: 12/12 hour light-dark cycle
  Temperature: 22±3° C.
  Relative Humidity: 30 to 70%
  Animals had continuous access to fresh, potable, uncontaminated drinking water.
  Feed: Normal chow diet [PURINA 5L79 from PMI Nutritional, USA]
Group, Designation and Dose Levels:

TABLE 1

Animal grouping and treatment details

| Groups | Group Description | Treatment Description | No. of animals |
|---|---|---|---|
| Group 1 | Normal Control (Without Exposure of Ischemia Reperfusion) | 0.5% Carboxy Methyl Cellulose Sodium (CMC) | 06 |
| Group 2 | Ischemia Reperfusion (I/R) Control (Exposure of Ischemia Reperfusion) | 0.5% CMC | 06 |
| Group 3 | Standard (Cerebroprotein hydrolysate (Tablet) + Exposure of Ischemia Reperfusion) | 9.3 mg/kg | 06 |
| Group 4 | (Agmatine Sulphate -AGM) + Exposure of Ischemia Reperfusion | 310 mg/kg | 06 |
| Group 5 | (Bio-optimized PEA) + Exposure of Ischemia Reperfusion | 372 mg/kg | 06 |
| Group 6 | (Agmatine Sulphate-AGM + Bio-optimized PEA) + Exposure of Ischemia Reperfusion | 310 mg/kg + 372 mg/kg | 06 |

Test Items, Vehicle and Formulation Details
  Test item: G4, G5, G6
  Dose: G4—310 mg/kg; G5—372 mg/kg; G6—310 mg/kg+372 mg/kg
  Route: Oral route (p.o)
  Frequency: Daily
Experimental Procedure:

Animals were divided into ten groups; each group consists of 6 animals. Group 1 was served as a Normal control and treated with vehicle 0.5% CMC; Group 2 was served as Ischemia Reperfusion control and treated with vehicle 0.5% CMC, whereas Group 3 was treated with standard product (Cerebroprotein hydrolysate). Group 4 and Group 5 received test sample AGM sulfate and test sample Bio-optimized PEA respectively. Group 6 was received test sample AGM sulfate and test Bio-optimized PEA in combination.

Treatment was given orally for 10 days. Test substances AGM (310 mg/kg), Bio-Optimized PEA (372 mg/kg), AGM+Bio-Optimized PEA (310 mg/kg+372 mg/kg), were administered orally for 10 days. At the end of the experimental period blood was collected for biochemical analyses and animals were sacrificed for histological analysis.

On 7th day, all the experimental animals, excluding Group 1, were exposed to ischemia followed by 72 hrs reperfusion along with treatment. After 72 hours of reperfusion, the animals were euthanized by isoflurane until breathing stopped. The rats were decapitated immediately and their brains were extracted for biochemistry and TTC staining.

The result of the test substances showed effective prevention of neuron cells from death caused by cerebral ischemia or reperfusion to protect from brain damage.

i. Induction of Cerebral Infarction:

Induction of Global cerebral ischemia/reperfusion was carried out using the standard method.

The rats were anaesthetized with an i.p. co-injection of ketamine (85 mg/kg) and xylazine (15 mg/kg) and a midline ventral incision was made in the throat. Right and left common carotid arteries were located and free from surrounding tissue and vagus nerve. A cotton thread was passed below each artery. Global cerebral ischemia was induced by occluding the carotid arteries with a knot. After 30 mins of global cerebral ischemia, the cotton thread was removed with the help of two knot releasers to allow the reperfusion of blood through carotid arteries for 72 hrs. All surgical procedure was carried out under aseptic and sterile condition.

ii. Tetrazolium Chloride Staining (TTC Staining):

The rats were anesthetized and received cardiac perfusion with 100 ml cold saline. The brains were carefully removed. The brains were frozen at −20° C. for 20 min, and then cut from the anterior pole into five coronal slices of 2 mm thickness. The slices were stained with 2% 2, 3, 5 triphenyltetrazolium chloride solution in the dark at 37° C. in an incubator for 30 min, and turned over every 5 min. A 10% buffered-formalin solution was used for fixation (24 h) prior to imaging. The normal brain tissue was stained red, whereas the ischemic area remained unstained.

iii. Statistical Analysis

The values were expressed in Mean±sem. The significance of in vivo data was analyzed by one way Anova followed by Dunnet test. P<0.05 was considered as significant.

RESULTS

TABLE 1

Effect of test substances on Rat body weight
Body Weight (gm)

| Group | Treatment | Basal | Week 01 |
|---|---|---|---|
| Group 1 | Normal Control (0.5% CMC) | 214.67 ± 0.76 | 225.33 ± 0.71 |
| Group 2 | Positive Control (0.5% CMC) | 214.50 ± 0.92 | 225.00 ± 0.68 |
| Group 3 | Standard (9.3 mg/kg) | 213.83 ± 0.95 | 224.67 ± 0.84 |
| Group 4 | Agmatine sulphate (310 mg/kg) | 215.00 ± 0.73 | 224.33 ± 0.42 |
| Group 5 | Bio-optimized PEA (372 mg/kg) | 214.17 ± 1.19 | 223.50 ± 1.38 |
| Group 6 | Agmatine sulphate (310 mg/kg) + Bio-optimized PEA (372 mg/kg) | 214.33 ± 0.88 | 223.40 ± 0.76 |

Values were expressed as mean ± SEM (n = 6), Statistical significance are compared between Ischemic Reperfusion control (Group 2) versus other treatment groups (G1, G3, G4, G5, G6) (* P Value < 0.05;  P Value < 0.001; * P Value < 0.0001).

TABLE 2

Effect of test substances on Rat Feed Consumption
Feed Consumption (gm)

| Group | Treatment | Week 01 |
|---|---|---|
| Group 1 | Normal Control (0.5% CMC) | 101.71 ± 1.43 |
| Group 2 | Positive Control (0.5% CMC) | 101.29 ± 1.27 |
| Group 3 | Standard (9.3 mg/kg) | 101.14 ± 0.91 |
| Group 4 | Agmatine sulphate (310 mg/kg) | 99.57 ± 1.19 |
| Group 5 | Bio-optimized PEA (372 mg/kg) | 99.86 ± 1.14 |
| Group 6 | Agmatine sulphate (310 mg/kg) + Bio-optimized PEA (372 mg/kg) | 98.43 ± 1.17 |

TABLE 3

Effect of test substances on Rat TNF alpha Level
TNF alpha Level (pg/ml)

| Group | Treatment | TNF alpha |
|---|---|---|
| Group 1 | Normal Control (0.5% CMC) | 71.17 ± 3.48 |
| Group 2 | Positive Control (0.5% CMC) | 172.17 ± 6.35 |
| Group 3 | Standard (9.3 mg/kg) | 109.00 ± 3.02*** |
| Group 4 | Agmatine sulphate (310 mg/kg) | 142.00 ± 1.53*** |
| Group 5 | Bio-optimized PEA (372 mg/kg) | 144.17 ± 4.34*** |
| Group 6 | Agmatine sulphate (310 mg/kg) + Bio-optimized PEA (372 mg/kg) | 130.83 ± 3.92*** |

Values were expressed as mean ± SEM (n = 6), Statistical significance are compared between Ischemic Reperfusion control (Group 2) versus other treatment groups (G1, G3, G4, G5, G6) (* P Value < 0.05;  P Value < 0.001; *P Value < 0.0001).

TABLE 4

Effect of test substances on Rat Interleukin - 6 Levels
Interleukin - 6 Levels (pg/ml)

| Group | Treatment | Interleukin - 6 |
|---|---|---|
| Group 1 | Normal Control (0.5% CMC) | 41.67 ± 1.37 |
| Group 2 | Positive Control (0.5% CMC) | 121.83 ± 1.65 |
| Group 3 | Standard (9.3 mg/kg) | 67.00 ± 1.21*** |
| Group 4 | Agmatine sulphate (310 mg/kg) | 91.39 ± 0.92*** |
| Group 5 | Bio-optimized PEA (372 mg/kg) | 92.56 ± 0.61*** |
| Group 6 | Agmatine sulphate (310 mg/kg) + Bio-optimized PEA (372 mg/kg) | 83.06 ± 1.28*** |

Values were expressed as mean ± SEM (n = 6), Statistical significance are compared between Ischemic Reperfusion control (Group 2) versus other treatment groups (G1, G3, G4, G5, G6) (* P Value < 0.05;  P Value < 0.001; *P Value < 0.0001).

DISCUSSION

Cerebral ischemia causes dizziness, double vision, difficulty in speaking or slurred speech, loss of body coordination and sometimes paralysis, while untreated will result in unconsciousness, permanent damage to the brain or death.

The present investigation demonstrated the neuroprotective activity of test substances against Global Ischemia Reperfusion Induced Brain Injury (Cerebral Infarction) in Wistar Rats. There was no significant change on Body weight in all the groups observed when compared with Ischemia Reperfusion Control group (G2) (Table 1).

Table 2 represents the Feed intake of rats, which did not show any significant changes when observed in all the groups in comparison with Ischemia Reperfusion Control group (G2).

Table 3 & FIG. 1 represent the TNF alpha levels showing significant decrease in the test substances treated group when compared with Ischemia Reperfusion Control group (G2).

Figure 2:
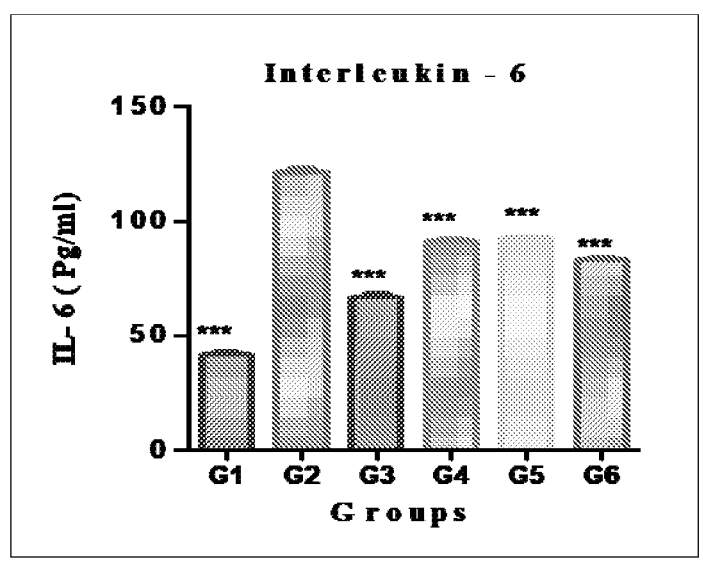
FIG. 2 illustrates the effect of test substances on Rat Interleukin-6 (IL-6) levels.

Interleukin-6 levels showed significant decrease in the test substances treated group when compared with Ischemia Reperfusion Control group (G2) (Table 4 & FIG. 2).

FIG. 5 represents the Tetrazolium chloride staining (TTC) of brain tissue of animals showing normal brain tissue was stained red, whereas ischemic area remained unstained.

CONCLUSION

In the present study, the model of global ischemia reperfusion induced brain injury (cerebral infarction) was performed in rats. The brain infarct area, biochemical parameters and histopathology of normal and treated rats with cerebral ischemia or reperfusion injury were investigated to find out how the test substances to protect and improve the brain function. The results showed that these test substances could significantly reduce relative inflammation in brain and rescue neural dysfunction effectively.

It is concluded that, the test substance i.e., combination of AGM+Bio-optimized PEA effectively prevents neuron cells from death caused by cerebral ischemia or reperfusion to protect from brain damage as compared to individual dose of AGM or Bio-optimized PEA.

We claim:

1. A synergistic nutritional composition, comprising:
an exogenous therapeutic blend; and
pharmaceutically acceptable excipients,
   wherein the exogenous therapeutic blend consists of a crystalline organoleptic agmatine sulfate and palmitoylethanolamide,
   wherein the crystalline organoleptic agmatine sulfate is present in a range of 400 to 600 mg of a total of the synergistic nutritional composition and the palmitoylethanolamide is present in a range of 200 to 400 mg of a total of the synergistic nutritional composition,
   wherein the synergistic nutritional composition is effective for treating ischemia-induced neuropathic pain in a human in need thereof, and
   wherein the neuropathic pain is central, peripheral, or both.

2. The synergistic nutritional composition as claimed in claim 1, wherein the palmitoylethanolamide is present in a micronized form with particle size in a range of 2 μm-6 μm.

3. The synergistic nutritional composition as claimed in claim 1, wherein the pharmaceutically acceptable excipients are selected from the group consisting of a diluent present in a range of 1 to 30%, a binder present in a range of 0.1 to 30%, a lubricant present in a range of 0.1 to 5.0%, a glidant present in a range of 0.1 to 5.0%, an additive present in a range of 1 to 10%, a surfactant present in a range of 0.1 to 5.0%, and a stabilizer present in a range of 0.1 to 10.0%, by a total weight of the synergistic nutritional composition.

* * * * *